United States Patent [19]

Haber et al.

[11] Patent Number: 4,804,370

[45] Date of Patent: Feb. 14, 1989

[54] DISEASE CONTROL SYRINGE HAVING A RETRACTABLE NEEDLE

[75] Inventors: Terry M. Haber, El Toro; William H. Smedley, Lake Elsinore; Clark B. Foster, El Toro, all of Calif.

[73] Assignee: Habley Medical Technology Corporation, Laguna Hills, Calif.

[21] Appl. No.: 202,676

[22] Filed: Jun. 6, 1988

Related U.S. Application Data

[63] Continuation of Ser. No. 51,392, Mar. 2, 1988, Pat. No. 4,770,655, which is a continuation-in-part of Ser. No. 25,419, Mar. 13, 1987.

[51] Int. Cl.⁴ .............................................. A61M 5/32
[52] U.S. Cl. ..................................... 604/195; 604/110
[58] Field of Search ............... 604/195, 198, 194, 196, 604/110

[56] References Cited

U.S. PATENT DOCUMENTS 3,306,290  2/1967  Weltman ......................... 604/195 X
4,542,749  9/1985  Caselgrandi et al. ............ 604/196 X
4,592,744  6/1986  Jagger et al. ....................... 604/192

Primary Examiner—John D. Yasko
Attorney, Agent, or Firm—Morland C. Fischer

[57] ABSTRACT

A disposable disease control syringe which reduces the frequency of accidental needle strikes to health care workers and prevents health-threatening reuse of the needle cannula by drug abusers. The syringe includes a cylinder having an open proximal end, a substantially closed distal end, and a retractable needle projecting through the distal end. A piston assembly having a detachable stem and a needle capturing receptacle moves axially and distally through the syringe cylinder to expulse fluid medication and to selectively engage the needle at the most distal aspect of the cylinder. The piston assembly is then withdrawn proximally through the cylinder, whereby to relocate the needle from the distal end to the proximal cylinder end. The needle capturing receptacle is locked at the proximal end of the syringe cylinder with the needle cannula retracted within and completely shielded by the cylinder. The stem is then detached from the piston assembly and discarded, thereby creating a disposal cartridge with the needle cannula rendered permanently irretrievable therewithin. Alternatively, the piston assembly can be driven distally through the cylinder for correspondingly moving the needle into contact with a puncture resistant shield located at the distal end of the cylinder, whereby the needle is axially collapsed and destroyed within the cylinder.

15 Claims, 4 Drawing Sheets

DISEASE CONTROL SYRINGE HAVING A RETRACTABLE NEEDLE

CROSS-REFERENCE TO RELATED APPLICATIONS

This application is a continuation of patent application Ser. No. 51,392 filed Mar. 2, 1988, now U.S. Pat. No. 4,770,655 which is a continuation-in-part of patent application Ser. No. 25,419 filed Mar. 13, 1987 pending.

BACKGROUND OF THE INVENTION

1. Field of the Invention

This invention relates to a disposable disease control syringe which is adapted to reduce the frequency of accidental and, in some cases, life threatening needle strikes while reducing instances of possible drug abuse and the spread of contagious disease by preventing reuse of the syringe by drug abusers.

2. Prior Art

Hypodermic syringes are used for a variety of injection procedures including the delivery of medicinal drugs to a recipient. However, once the injection procedure is completed and the syringe cylinder emptied, problems may arise as a consequence of failing to properly and adequately dispose of the syringe. By way of a first example, the syringe may be used to treat a patient having a communicable disease. To prevent reuse, the hypodermic needle is sometimes broken before the syringe is discarded. Health care workers are susceptible to accidental and potentially infectious needle strikes due to the careless handling of the hypodermic needle when breaking the needle or disposing of the syringe after use. The resulting mini-accidents caused by an accidental needle strike typically require a blood test for such diseases as AIDS and hepatitis. The corresponding cost and inefficiency of testing health care workers who have received an inadvertent needle strike result in considerable waste, which may be particularly damaging to a health care facility striving for economy and efficiency. By way of a second example, drug users have been known to rummage through the trash of a health facility in an effort to find emptied syringes which have been discarded after use. Such syringes are often reused in an illicit capacity, whereby to promote drug abuse and the possible spread of contagious disease.

The following U.S. Pat. Nos. provide examples of syringes having a hypodermic needle which may be withdrawn into the syringe cylinder after use:

2,722,215; Nov. 1, 1955
4,026,287; May 31, 1977
4,507,117; Mar. 26, 1985
4,650,468; Mar. 17, 1987

The vast majority of known syringes have no means by which a used hypodermic needle may be rendered permanently irretrievable within and shielded by the syringe cylinder, so that the syringe and needle are not reusable. That is to say, little is available to prevent the needle from being completely removed from the syringe cylinder and/or from being returned to an outwardly projecting position from the cylinder by which to execute another injection procedure. Consequently, the syringe and/or the needle, may be reused. Moreover, a greater opportunity exists to handle a used needle which has been removed from or returned to the cylinder, so as to disadvantageously contribute to an accidental needle strike and the possible spread of disease.

SUMMARY OF THE INVENTION

In general terms, a disposable disease control syringe is disclosed which overcomes the problems inherent in a conventional syringe by reliably reducing the frequency of accidental needle strikes among health care workers while preventing reuse of the needle by drug users. The syringe includes a cylinder or barrel having a substantially closed distal end and an open proximal end. A first end of a needle projects outwardly from the distal cylinder end, by which a fluid may be injected or infused in the conventional manner. A second end of the needle extends into the interior of the cylinder and terminates at a relatively large needle catch.

The syringe also includes a piston which is adapted for reciprocal and axial movement through the syringe cylinder. The piston comprises the detachable connection of an elongated piston stem to a sealing and locking assembly. An elastomeric seal, formed at one end of the sealing and locking assembly, functions as a plunger head when the piston is moved axially through the syringe cylinder during a fluid injection procedure. The seal is mounted around a plurality of flexible legs which define a needle capturing receptacle therebetween. When the piston is moved through the syringe cylinder at the conclusion of a fluid injection procedure, the elastomeric seal is compressed against the most distal aspect of the cylinder, such that the needle capturing receptacle is advanced axially into engagement with the needle catch. The needle catch is thereby snapped into receipt by the receptacle.

The piston stem is now withdrawn through the open proximal end of the syringe cylinder, whereby to relocate the needle from the distal end to the proximal cylinder end, such that the needle cannula is fully retracted into the interior of the syringe cylinder. According to a first embodiment of the invention, the sealing and locking assembly is permanently locked across the proximal end of the cylinder to both block the removal of the needle from the cylinder and prevent any return of the needle from the proximal end to the distal cylinder end. The piston stem is then detached from the piston by breaking the stem away from the sealing and locking assembly. According to a second embodiment of the invention, a puncture resistant shield is located at the distal end of the cylinder, and the needle capturing receptacle is provided with a configuration by which to cant the needle relative to the longitudinal axis of the cylinder when the needle is relocated to the proximal cylinder end. The piston stem may then be driven axially and distally through the cylinder for moving the canted needle into contact with the puncture resistant shield to axially collapse, and thereby destroy, the needle within the cylinder.

The syringe may then be discarded in a normal fashion. However, by virtue of the present invention, the resulting cartridge is rendered safe, such that the used needle is completely shielded by and rendered totally irretrievable within the syringe cylinder. Accordingly, the syringe cannot be reused. Moreover, the used syringe is in a condition to permit safe disposal without requiring handling or cutting of the needle as has heretofore been necessitated as a consequence of many conventional syringe assemblies.

DESCRIPTION OF THE PREFERRED EMBODIMENT

Figure 1:
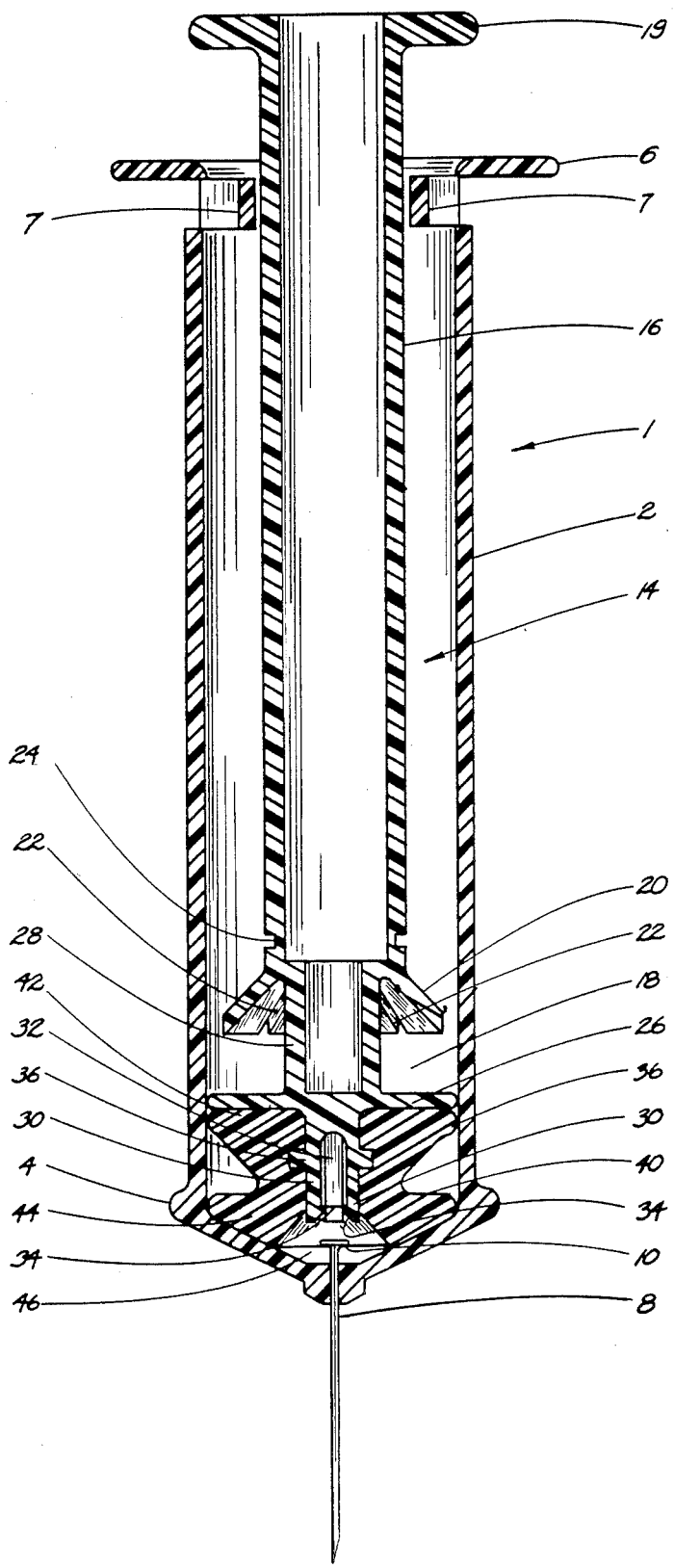
FIG. 1 is a cross-section of a syringe which forms one embodiment of the present invention showing a piston moved to a distal end of the syringe cylinder.

The disease control syringe having a retractable needle which forms the present invention is best described while referring to the drawings. In FIG. 1, there is shown the syringe 1 including a generally cylindrical cylinder or barrel 2 having an open proximal end and a closed distal end. An anti-slip flange 4 is disposed around the distal end and a major flange 6 is disposed around the proximal end of the cylinder 2. The use of the flanges 4 and 6 will soon be described. A pair of internal locking tabs 7 are formed at the proximal end of cylinder 2 below the major flange 6 thereof. In the embodiment shown in FIG. 1, the locking tabs of syringe 1 are formed by compressing opposite sides of the cylinder 2 to form an area of reduced diameter adjacent the opening at the proximal end thereof. However, it is to be understood that the locking tabs may be formed by any suitable means to establish an area of reduced diameter at the proximal cylinder end. An opening is formed in the closed distal end of syringe cylinder 2. The opening is sized to receive the cannula of a hollow needle 8 therethrough during the manufacture of the syringe 1. The needle cannula is retained in a tight fit within the distal hole of cylinder 2. Needle 8 has a sharp cutting surface formed at a distal end thereof and an enlarged, generally annular catch 10 formed at the proximal end. The cutting surface of needle 8 projects outwardly from the cylinder 2, and the needle catch 10 is located at the distal aspect of cylinder 2 to perform an important function which will be described in greater detail hereinafter.

Located within and adapted for reciprocal axial movement through the cylinder 2 is a piston 14. Piston 14 comprises the detachable connection of an elongated stem 16 to a sealing and locking assembly 18. The piston stem 16 is preferably, but not necessarily, hollow to facilitate a quick and relatively easy detachment of the stem 16 from the sealing and locking assembly 18 (in a manner to be described in greater detail when referring to FIG. 3). Formed around a proximal end of the stem 16 is a flange 19. Stem 16 is connected at the distal end thereof to a conical locking skirt 20 which is formed of a resilient material. The skirt 20 may have a plurality of slots 22 formed therealong to create a series of flexible locking fingers. The stem 16 and locking skirt 20 are connected to one another at opposite sides of a narrow groove 24 which is formed around the periphery of stem 16 to provide the stem with an area of reduced cross-section to thereby facilitate the detachment of the stem 16 from the sealing and locking assembly 18.

The sealing and locking assembly 18 includes a locking flange 26 which is coextensively connected to and spaced distally from the conical skirt 20 by way of a neck portion 28. Coextensively formed with and extending distally from the locking flange 26 are one or more pairs of oppositely disposed, flexible legs 30 between which is formed a hollow receptacle 32 for selectively capturing the catch 10 of the needle 8. That is to say, the needle 8, the catch 10 thereof, and the hollow needle capturing receptacle 32 are concentrically aligned with one another so that the needle catch 10 may be snapped into receipt by the receptacle 32 when piston 14 is moved to the most distal aspect of syringe cylinder 2 (best illustrated in FIG. 2).

Extending into the receptacle 32 from each of the flexible legs 30 is a tapered lip 34. As will be disclosed in greater detail when referring to FIG. 2, the lip portions 34 of legs 30 are snapped into engagement with the needle catch 10 whereby to permanently retain the needle catch within the receptacle 32 and prevent the withdrawal of catch 10 from receptacle 32.

Extending laterally from each of the legs 30 is a seal retaining flange 36. An elastomeric seal 40 is mounted upon the legs 30 and against the locking flange 36. The seal retaining flange 36 engages the seal and prevents the removal thereof during a displacement of the piston 14 through cylinder 2.

The elastomeric seal 40 includes a proximally extending base 42 which lies adjacent and is supported by the locking flange 26. Seal 40 also includes a distally extending sealing head 44 which is shaped so as to form a fluid-tight seal against the closed distal end of the cylinder 2 when the sealing and locking assembly 18 of piston 14 is moved to the most distal aspect of the syringe 1. A centrally disposed pocket 46 is formed through the sealing head 44 of seal 40 to permit the needle catch 10 of the needle 8 to be snapped into engagement with the lips 34 of legs 30 at needle capturing receptacle 32.

Figure 2:
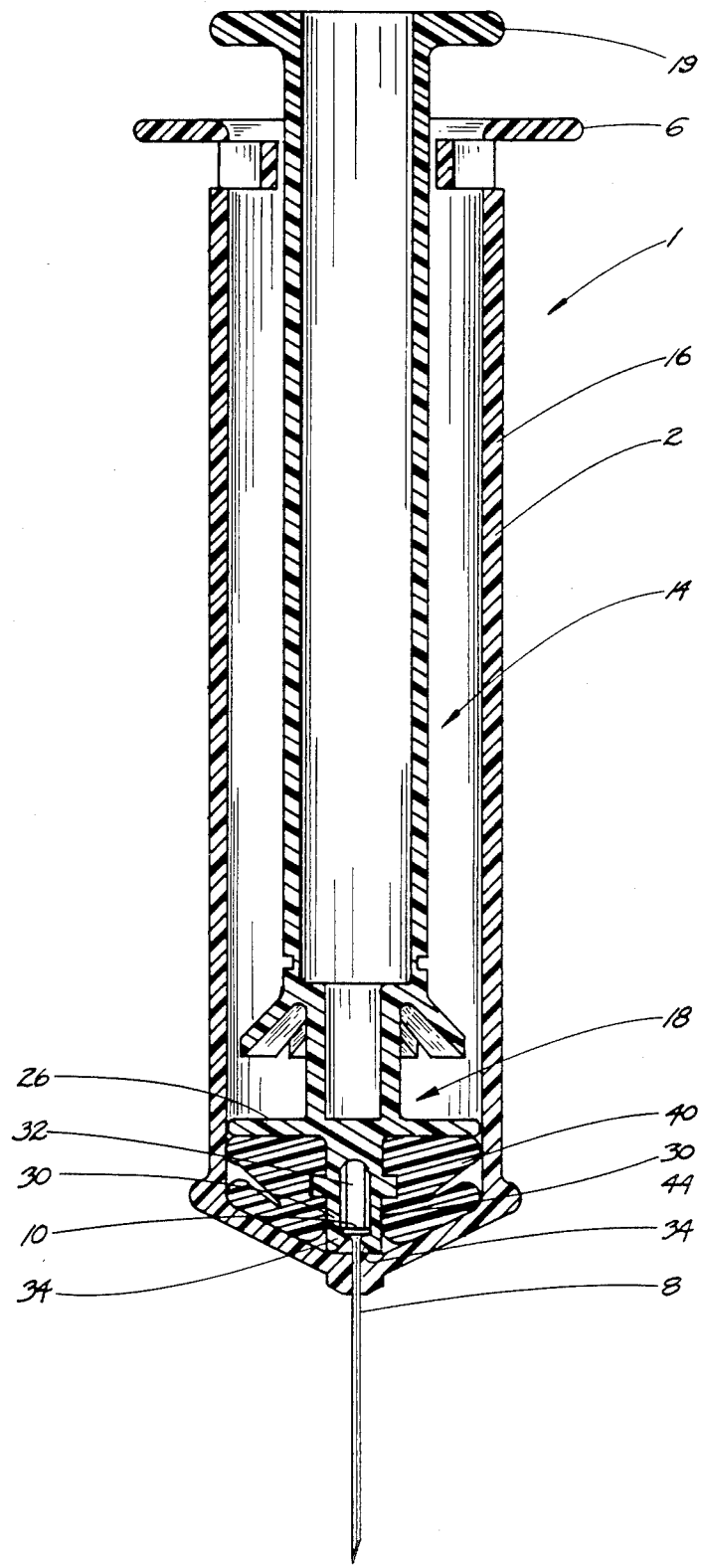
FIG. 2 is a cross-section of the syringe of FIG. 1 showing the piston engaging a needle at the most distal aspect of the syringe cylinder.
Figure 3:
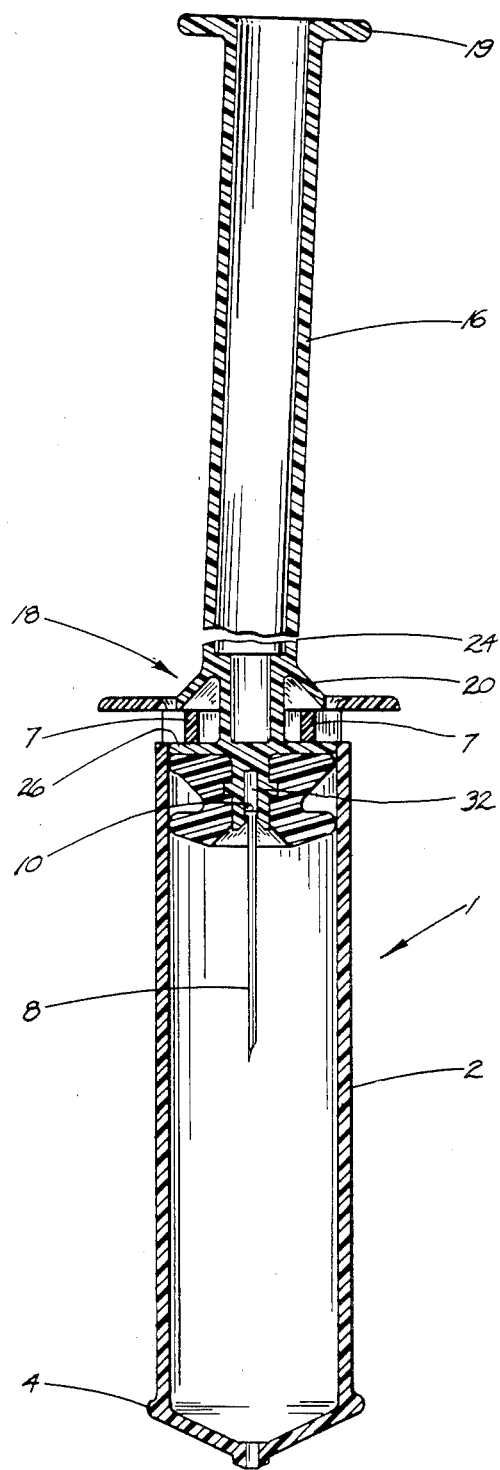
FIG. 3 is a cross-section of the syringe of FIG. 1 showing the needle relocated from the distal end to a proximal end of the syringe cylinder.

The operation of the disease control syringe 1 of the present invention is now described while referring to FIGS. 1–3 of the drawings. Initially, the needle 8 of the syringe 1 of FIG. 1 is moved into fluid communication with a fluid drug supply (not shown). The syringe 1 is infused with fluid medication in a conventional manner by grasping the cylinder 2 behind the anti-slip flange 4 and pulling the stem flange 19 of piston stem 16 to withdraw the piston 14 proximally and axially through the cylinder 2. Once the syringe is infused with medication, a conventional injection procedure may be executed by depressing the stem flange 19 and driving the piston distally through the cylinder 2.

At the conclusion of the injection procedure, and referring now to FIG. 2 of the drawings, the piston 14 is moved completely and axially through the cylinder 2 of syringe 1. The sealing and locking assembly 18 of piston 14 is thereupon moved to the most distal aspect of the syringe 1, whereby the sealing head 44 of elastomeric seal 40 is located flush against the closed distal end of cylinder 2. Next, the syringe 1 is supported at the major flange 6 thereof and the piston 14 is depressed distally while applying an axial force against the flange 19 of piston stem 16. Such axial force is transmitted from the stem 16 to the elastomeric seal 40 by way of the locking flange 46 upon which seal 40 is seated. Because of the resiliency of the seal 40, the sealing head 44 thereof is moved towards and compressed against the closed distal end of syringe cylinder 2. The compression and distal displacement of sealing head 44 correspondingly advances the flexible legs 30 of sealing and locking assembly 18 into engagement with the catch 10 of needle 8.

More particularly, the movement of the tapered lips 34 of the flexible legs 30 into engagement with the needle catch 10 causes a slight clockwise rotation and separation of the legs 30 so as to permit the catch 10 to be snapped into receipt by the needle capturing receptacle 32. After the needle catch 10 is moved past the lips 34 and into receptacle 32, the flexible legs 30 are automatically rotated counterclockwise to establish a positive locking feature for preventing the removal of the needle catch 10 from receptacle 32. That is, the lips 34 of legs 30 form shoulders or stops against which the needle catch 10 is seated when the catch is received within needle capturing receptacle 32. Such shoulders or stops establish a sufficiently narrow exit from cylinder 2 between opposing legs 30 to permanently prevent any removal of the needle catch 10 outwardly from the receptacle 32.

In FIG. 3 of the drawings, the needle 8 (with the catch 10 thereof permanently retained within needle capturing receptacle 32) is retracted from the distal end of cylinder 2 of syringe 1 and relocated at the proximal end thereof. The syringe cylinder 2 is grasped behind the anti-slip flange 4, and the flange 19 of piston stem 16 is withdrawn proximally (in the direction of the reference arrows) and outwardly of the cylinder 2.

More particularly, the stem 16 is moved through the open proximal end of cylinder 2, whereby the conical locking skirt 20 is correspondingly moved into engagement, and then past, the internal locking tabs 7. The movement of the resilient locking skirt 20 into engagement with locking tabs 7 causes a compression of the locking skirt 20 to permit the skirt to be moved past the locking tabs. Once the resilient locking skirt 20 is moved past locking tabs 7 and through the open proximal end of cylinder 2, the previously compressed locking skirt 20 is relaxed and automatically returned to its pre-compressed shape to prevent the return of the locking skirt to the interior cylinder 2 via the open proximal end thereof. That is to say, the relatively large diameter base of conical skirt 20 is seated upon the locking tabs 7. As previously disclosed when referring to FIG. 1, the locking tabs 7 establish a relatively narrow diameter opening at the proximal end of cylinder 2 to form a stop, whereby to block the return of locking skirt 20 and, therefore, the piston stem 16 to the interior of cylinder 2.

What is more, relocating the needle 8 to the proximal end of cylinder 2 correspondingly moves the locking flange 26 axially through the cylinder 2 and into engagement with locking tabs 7 across the proximal end of the cylinder. However, the locking tabs 7 act as a stop to prevent the removal of the locking flange 26 (as well as the needle capturing chamber 32 at which needle 8 is permanently retained) from the proximal end of cylinder 2. Therefore, the needle 8 projects from the proximal end and is located completely within the walls of the cylinder 2 of syringe 1.

When the piston stem 16 is completely withdrawn from the syringe cylinder 2 and the needle 8 is relocated from the distal to the proximal cylinder end, the stem 16 may be detached from the sealing and locking assembly 18. With the locking skirt 20 and the locking flange 26 of the sealing and locking assembly 18 immovably disposed at opposite sides of the locking tabs 7 and across the proximal end of cylinder 2, a sufficient bending force is exerted upon the piston stem 16 to fracture the stem along the groove 24 formed around the periphery thereof. The piston stem 16 is then discarded. However, the locking skirt 20 and the locking flange 26 remain anchored at opposite sides of the locking tabs 7 to seal off the proximal end of cylinder 2 and thereby block access to the needle 8 at the interior of the cylinder. More particularly, the needle cannot be removed from the cylinder 2, because locking tabs 7 prevent both the movement of locking flange 26 therepast and the withdrawal of needle 8 from cylinder 2. Moreover, the syringe cylinder cannot be reused, because locking tabs 7 also prevent both the movement of conical locking skirt 20 therepast, and the return of the needle 8 to the distal end of cylinder 2. Accordingly, the needle capturing receptacle 32 is locked at its final position in cylinder 2 (with the needle catch 10 permanently retained in receptacle 32), so as to create a self-contained disposal cartridge with the needle cannula shielded and rendered irretrievable therewithin.

Figure 5:
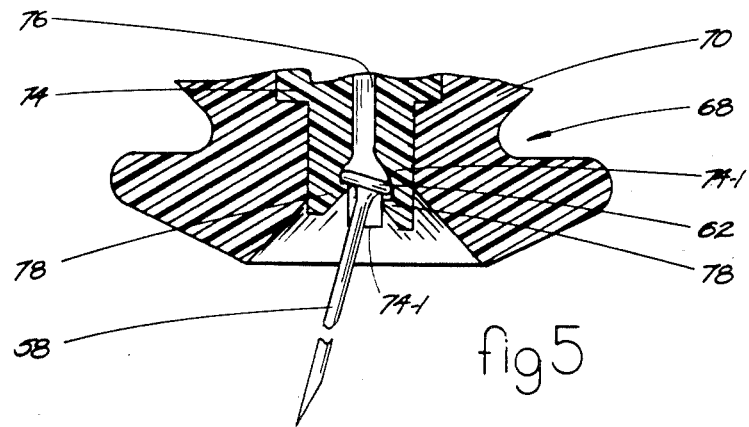
FIG. 5 shows a detailed enlargement of the canted needle attached to the piston of the syringe of FIG. 4.
Figure 4:
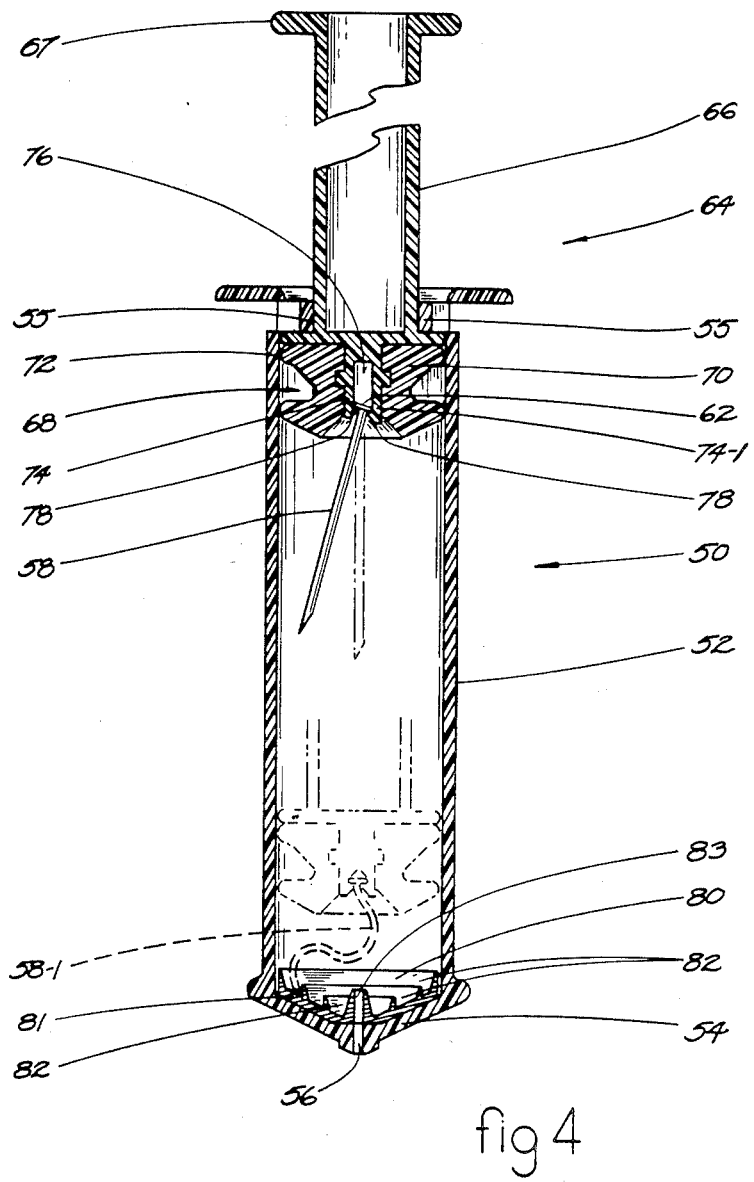
FIG. 4 is a cross-section of a syringe which forms a second embodiment of the present invention showing a canted needle permanently attached to a piston and located at a proximal end of the syringe cylinder.

FIGS. 4 and 5 of the drawings illustrate a disease control syringe 50 having a retractable needle and means by which to destroy the needle after use, so that the destroyed needle may be irretrievably shielded within the syringe cylinder, and the syringe can be rendered safe for handling and disposal. In FIG. 4, there is shown the syringe 50 including a generally cylindrical cylinder or barrel 52 having an open proximal end and a substantially closed distal end wall 54. A pair of internal piston stops 55 are formed below the open proximal end of cylinder 52. In the embodiment shown in FIG. 4, the piston stops 55 of syringe 50 are formed by compressing opposite sides of the cylinder 52 to form an area of reduced cylinder diameter. An opening 56 is formed through the distal end wall 54 of cylinder 52 to receive the cannula of a hollow hypodermic needle 58 during the manufacture of the syringe. The needle cannula is removably retained by friction within the distal hole 56 of cylinder 52. Needle 58 has a sharp tissue penetrating surface formed at a distal end thereof and an enlarged, generally annular needle catch 62 formed at the proximal end. In the assembled relationship (and similar to that shown previously when referring to FIG. 1), the distal tissue penetrating end of needle 58 projects outwardly from the cylinder 52, and the needle catch 62 is spaced proximally from distal end wall 54 of cylinder 52 at the distal aspect of syringe 50.

Located within and adapted for reciprocal, axial movement through the cylinder 52 is a piston 64 comprising an elongated, proximally oriented piston stem 66 and a distally oriented sealing and locking assembly 68. The sealing and locking assembly 68 of piston 64 includes an elastomeric sealing head 70 that is seated against a flat locking flange 72. Locking flange 72 extends transversely across the cylinder 52 at the interface of the piston stem 66 with the sealing and locking assembly 68.

Coextensively formed with and extending distally from the locking flange 72 are a plurality (e.g. four) of oppositely disposed flexible legs 74 and 74-1. The sealing head 70 of sealing and locking assembly 68 is supported by the legs 74 and 74-1 for axial and reciprocal movement through the cylinder 52 with piston 64. A hollow receptacle 76 for selectively capturing the needle catch 62 of needle 58 is established in the space between opposing pairs of legs 74 and 74-1. The needle 58, the catch 62 thereof, and the receptacle 76 are coaxially aligned with one another, so that the needle catch 62 may be received within the receptacle 76 when piston 64 is moved axially to the most distal aspect of the syringe cylinder 52. Projecting into receptacle 76 from each of the flexible legs 74 and 74-1 is a tapered lip 78. The lips 78 of legs 74 and 74-1 are snapped into engagement with the needle catch 62 to permanently retain the needle catch within receptacle 72 and prevent the detachment of needle 58 from piston 64.

As is best shown in FIG. 5, one or more (e.g. in this case, two) of the flexible legs 74-1 which define needle capturing receptacle 76 are offset from the other legs 74. That is to say, legs 74-1 are longer than the remaining legs 74, such that the respective lips 78 of legs 74-1 are disposed distally from the lips of legs 74. Accordingly, opposing lips 78 of the legs 74 and 74-1 are aligned on an angle relative to one another. The advantage of the aforementioned offset configuration of legs 74 and 74-1 will soon be explained.

Located adjacent the interior of the distal end wall 54 of syringe cylinder 52 is a needle locating shield 80. Needle locating shield 80 is formed from a suitable puncture resistant material, such as metal, or the like. Shield 80 comprises a generally conical base 81 having a series of coaxially aligned, annular ribs 82 extending proximally therefrom. A central opening 83 is formed through the needle locating shield (to be aligned with the opening 56 in the distal end wall 54 of syringe cylinder 52), so that the needle 58 may be received therethrough during manufacture of the syringe 50. Needle locating shield 80 may be retained at the most distal aspect of syringe cylinder 52 by means of friction. In the alternative, the conical base 81 of shield 80 may be secured (e.g. cemented) to the distal end wall 54 of cylinder 52.

The operation of the disease control syringe 50 for destroying a used needle 58 and for shielding the needle completely within the syringe cylinder 52 is now described while continuing to refer to FIGS. 4 and 5 of the drawings. With needle 58 extending outwardly from the hole 56 in the distal end wall of cylinder 52, the syringe 50 is infused with a supply of fluid medication (in a manner similar to that which was previously described when referring to FIG. 1). A conventional injection procedure may be executed by depressing the proximal flange 67 of piston stem 66, thereby driving piston 64 axially and distally through cylinder 52. The sealing and locking assembly 68 of piston 64 is moved to the distal aspect of the syringe 50, whereby the elastomeric sealing head 70 of assembly 68 is located adjacent the distal end wall 54 of cylinder 52, and fluid is expulsed through needle 58. An additional axial force is then applied to the proximal flange 67 of piston stem 64, whereby the sealing head 70 of sealing and locking assembly 68 is compressed against the needle positioning shield 80 at the distal end wall 54 of cylinder 52 (in a manner similar to that which was previously disclosed when referring to FIG. 2). The compression and distal advancement of sealing head 70 against shield 80 correspondingly advances the flexible legs 74 and 74-1 of sealing and locking assembly 68 into contact with the catch 62 of needle 58, whereby the catch is received within the needle capturing receptacle 76.

More particularly, the needle catch 62 is moved past and snapped into engagement with the lips 78 of legs 74 and 74-1, such that catch 62 is permanently retained within needle capturing receptacle 76. The lips 78 form shoulders or stops against which the needle catch 62 is seated within receptacle 76 to provide a positive locking feature for preventing the removal of the catch 62 outwardly from the receptacle. After the injection procedure has been completed, and with the needle catch 62 permanently retained within needle capturing receptacle 76 so that the needle 58 is fixedly attached to piston 64, the used needle 58 is retracted from the distal end of cylinder 52 for relocation to a relatively proximal position therewithin. That is to say, and as is illustrated in FIG. 4, the proximal flange 67 of piston stem 66 is grasped and the piston 64 is withdrawn proximally through and outwardly of the cylinder 62 to overcome the friction fit between needle 58 and the hole 56 at the distal end wall 54 of cylinder 52, such that needle 58 is withdrawn into the interior of cylinder 52 through the opening 83 in needle locating shield 80.

Relocating the needle 58 toward the proximal end of syringe cylinder 62 correspondingly moves the locking flange 72 of piston 64 axially and proximally through cylinder 52 and into engagement with the piston stops 55. The piston stops 55 block the movement of the locking flange 72 therepast, whereby to prevent a removal of the sealing and locking assembly (as well as the needle capturing receptacle 76 in which the catch 62 of needle 58 is permanently retained) from the syringe 50.

By virtue of the offset configuration of the flexible legs 74 and 74-1 (with the lips 78 of certain legs 74-1 spaced distally from the lips of the remaining legs 74), the used needle 58 will be canted or slanted relative to the vertical when the needle catch 62 is received within needle capturing receptacle 76 and the needle is relocated from a distal to a relatively proximal position within cylinder 52. Thus, the needle is now misaligned with respect to both the opening 83 in shield 80 and the hole 56 in distal end wall 54. The piston 64 is once again moved axially and distally through the syringe cylinder 52, whereby to correspondingly advance needle 58 towards the needle locating shield 80. However, the canted alignment of needle 58 will prevent the needle from being relocated through the opening 83 and the hole 56.

More particularly, and as shown in phantom in FIG. 4, the distal tissue penetrating end of the used needle 58 will be received against the puncture resistant base 81 between a pair of successive annular ribs 82 of the needle locating shield 80. The ribbed surfaces of shield 80 prevent the lateral displacement of the needle 58 along the base 81 to thereby assure that the needle will remain completely surrounded by the syringe cylinder 52, while eliminating the possibility that the distal end of needle 58 might be returned to the outwardly extending position (of FIG. 1) relative to cylinder 52.

The continued distal advancement of piston 64 through cylinder 52 will cause needle 58 to be compressed between the locking flange 72 and the puncture resistance base 81 of needle locating shield 80. Accordingly, the used needle is axially collapsed or bent, but not snapped, and permanently destroyed within the cylinder 52. The bent needle is shown in phantom and designated by reference numeral 58-1.

It should now be apparent that, by virtue of the invention illustrated in FIGS. 4 and 5, the bent needle 58-1 cannot be removed from the cylinder 52 and the syringe 50 cannot be reused. More particularly, the needle 58-1 cannot be removed from the open proximal end of the syringe cylinder 52, because piston stops 55 prevent the movement of the locking flange 72 therepast, whereby to limit the proximal displacement of the piston 64 through the cylinder 52. What is more, access to the interior of the cylinder 52 is blocked, so that the destroyed needle 58-1 is completely shielded by the cylinder and rendered irretrievable therewithin. Accordingly, a disposal cartridge is created, so that the syringe 50 may be safely handled and discarded while avoiding an accidental needle strike and the possible spread of a contagious disease.

By virtue of the present invention, a needle can be retracted and sealed within the syringe cylinder, whereby to render an emptied syringe safe from accidental needle strikes by eliminating the need for health care workers to either handle or cut the needle as has heretofor been required with conventional syringes. In addition, reuse of the syringe for possible drug related purposes is prevented, inasmuch as the needle is permanently destroyed and/or irretrievable locked within the syringe cylinder. Thus, the spread of contagious disease as has been caused, in the past, by either an accidental needle strike or the reuse of a contaminated syringe by a drug abuser may be avoided.

It will be apparent that while a preferred embodiment of the invention has been shown and described, various modifications and changes may be made without departing from the true spirit and scope of the invention.

Having thus set forth a preferred embodiment of the invention, what is claimed is:

1. A syringe comprising a hollow cylinder having a substantially closed distal end and an open proximal end and a retractable needle communicating with the interior of said cylinder and positioned to extend outwardly through the distal end of cylinder via a distal hole so that an injection can be administered, said syringe also comprising:
   means movable through said cylinder for engaging said needle at the distal end of said cylinder and for retracting said needle from said distal hole and moving said needle towards the proximal end of said cylinder such that said needle is canted relative to the longitudinal axis of said cylinder, the canted alignment of said needle preventing the return of said needle to said distal hole in the event that said needle is moved back towards the distal end of said cylinder.

2. The syringe recited in claim 1, wherein said movable means for engaging and retracting said needle is a piston assembly adapted for axial and reciprocal movement through said cylinder.

3. The syringe recited in claim 2, wherein said piston assembly has means for engaging said needle at the distal end of said cylinder and canting said needle relative to the longitudinal axis of said cylinder when said needle is retracted from said distal hole and moved towards the proximal end of said cylinder.

4. The syringe recited in claim 3, wherein the means of said piston assembly for engaging said needle is a needle capturing receptacle formed at one end of said piston assembly.

5. The syringe recited in claim 4, wherein said needle has a cutting surface formed at one end thereof and projecting outwardly from said cylinder for penetrating the skin of a patient and a needle catch formed at the opposite end and spaced inwardly from the distal end of said cylinder, said piston assembly engaging said needle when said piston assemblly is moved through said cylinder such that said needle catch is received within said needle capturing receptacle.

6. The syringe recited in claim 5, wherein said needle capturing receptacle has means for canting said needle when said needle catch is received therein and said needle is retracted from said distal hole and moved towards the proximal end of said cylinder.

7. The syringe recited in claim 6, wherein said needle capturing receptacle is located between a plurality of flexible legs, said legs having means for retaining said needle catch in the receptacle therebetween and preventing the withdrawal of said needle catch therefrom.

8. The syringe recited in claim 7, wherein at least one of said flexible legs is longer than other ones of said legs, such that said needle is canted when said needle catch is received within said needle capturing receptacle and said needle is retracted from said distal hole and moved towards the proximal end of said cylinder.

9. A syringe comprising a hollow cylinder having proximal and distal ends and a retractable needle extending through said distal end and communicating with the interior of said cylinder, said syringe comprising:
   means for engaging said needle at the interior of said cylinder and for retracting said needle from the distal end of said cylinder for relocation towards the proximal end of said cylinder; and
   means located at the interior of said cylinder for bending said needle after said needle has been retracted and relocated.

10. The syringe recited in claim 9, wherein said means for engaging and retracting said needle is a piston assembly which is movable axially and reciprocally through said cylinder.

11. The syringe recited in claim 9, wherein said means for bending said needle is connected to the distal end of said cylinder.

12. The syringe recited in claim 9, wherein said means for bending said needle includes needle puncture resistant means connected to said cylinder at the interior thereof, said needle engaging means moving said needle into contact with said puncture resistant means for bending said needle.

13. The syringe recited in claim 12, wherein said needle puncture resistant means is a shield located at the distal end of said cylinder.

14. The syringe recited in claim 13, wherein said shield includes a plurality of concentrically aligned ribs, said needle being moved into contact with said shield between an adjacent pair of said ribs.

15. The syringe recited in claim 9, wherein said needle has a cutting surface formed at one end thereof and extending outwardly from said cylinder for penetrating the skin of a patient and a needle catch formed at the opposite end and spaced inwardly from the distal end of said cylinder, said needle engaging means engaging said needle at said needle catch thereof.

* * * * *